United States Patent [19]

Marquez et al.

[11] Patent Number: 5,378,250

[45] Date of Patent: * Jan. 3, 1995

[54] PROCESS FOR PRODUCTION OF AN ETHER-RICH ADDITIVE

[75] Inventors: Marco A. Marquez, Caracas; Jose C. Gonzalez; Victor J. Degouveia, both of San Antonio de Los Altos; Carmelo Bolivar, Caracas; Orlando Leal, Caracas; Francisco Yanez, Caracas, all of Venezuela

[73] Assignee: Intevep, S.A., Caracas, Venezuela

[*] Notice: The portion of the term of this patent subsequent to May 11, 2010 has been disclaimed.

[21] Appl. No.: 60,736

[22] Filed: May 10, 1993

Related U.S. Application Data

[63] Continuation-in-part of Ser. No. 847,194, Mar. 6, 1992, Pat. No. 5,210,326.

[51] Int. Cl.$^6$ .......................... C10L 1/18; B01J 38/56; B01J 20/34; C10G 25/00
[52] U.S. Cl. ................................. 44/447; 44/448; 44/449; 208/91; 208/299; 502/29; 502/31; 502/38; 502/51; 568/687
[58] Field of Search .......................... 502/31, 51, 30, 29, 502/38; 568/697, 698, 699; 44/447, 448, 449

[56] References Cited

U.S. PATENT DOCUMENTS

| | | | |
|---|---|---|---|
| 2,754,344 | 7/1956 | Weatherly | 502/31 |
| 4,390,413 | 6/1983 | O'Rear et al. | 568/697 |
| 4,795,545 | 1/1989 | Schmidt | 208/91 |
| 4,846,962 | 7/1989 | Yao | 208/31 |
| 5,120,881 | 6/1992 | Rosenfeld et al. | 568/697 |
| 5,210,326 | 5/1993 | Marquez et al. | 568/697 |

Primary Examiner—Paul E. Konopka
Attorney, Agent, or Firm—Bachman & LaPointe

[57] ABSTRACT

A process for the production of an ether-rich additive for gasoline, and more particularly, the production of MTBE, TAME and mixtures thereof from light hydrocarbon streams comprising passing the light hydrocarbon stream, preferably from an FCC feedstock, through a superactivated porous particulate medium so as to remove nitrogen compounds, mercaptan and water prior to contacting the feedstock with a catalyst under etherification process conditions. The present invention further includes a process for regenerating the spent superactivated mediums used for purifying the feedstock employed in the process for the production of ether-rich additives for gasoline.

24 Claims, 5 Drawing Sheets

PROCESS FOR PRODUCTION OF AN ETHER-RICH ADDITIVE

This application is a continuation-in-part of co-pending and commonly assigned U.S. patent application No. 07/847,194, filed Mar. 6, 1992, now U.S. Pat. No. 5,210,326.

BACKGROUND OF THE INVENTION

The present invention relates to a process for the production of ether-rich additives for gasoline, and, more particularly, the. production of MTBE, TAME or mixtures thereof from light hydrocarbon streams.

MTBE, TAME or mixtures thereof are used extensively as fuel extenders and octane value improving agents in the production of unleaded gasoline. Generally, but for the inclusion of such fuel extenders and octane value improving agents, acceptable octane values can only be obtained by varying the compounding additives in the gasoline, that is, increasing the lead content of the gasoline. The desirability of lead free gasolines is clearly recognized. Lead additives in gasolines result in the emission of pollutants in exhaust gases from internal combustion engines thereby contributing to overall environmental pollution. The employment of substitutes for lead in gasoline compounds which improve the octane value of the gasoline will lead to a cleaner burning gasoline thereby improving air quality and the overall environmental condition.

There are many processes developed in the prior art for producing MTBE (methyl t-butyl ether) and TAME (methyl t-amyl ether). Typical etherification processes are disclosed in U.S. Pat. Nos. 5,001,292; 4,925,455; 4,827,045; and U.S. Pat. No. 4,830,635 to Harandi et al. Other known processes include that disclosed in U.S. Pat. No. 4,025,989 to Hagan et al. For the most part, these known processes for preparing ethers as additives for gasoline comprise reacting a primary alcohol, such as methanol, with an olefin having a double bond on a tertiary carbon atom, such as, isobutylene and isopropentene. It is known in the prior art to react the alcohol and the olefin in the presence of a catalyst. Suitable known catalysts include Lewis acids (sulfuric acid) and organic acids (alkyl and aryl sulfonic acids). A particularly suitable catalyst for these reactions are ion exchange resins in their acid form of the type marketed under the trademark "AMBERLIST 15" which is a trademark of Rohm and Haas, or Bayer product K2631. While many hydrocarbon feedstocks may be used for the manufacture of MTBE and TAME it is particularly useful in the petroleum refining operation to process MTBE and TAME from light hydrocarbon streams resulting from fluid catalytic cracking (FCC) refinery operations. When processing FCC hydrocarbon streams under etherification conditions so as to form MTBE and TAME it has been found that the catalysts used in the process are rapidly poisoned, that is, the catalysts are deactivated. As the catalyst materials used in known processes are relatively expensive, the foregoing problem of catalyst deactivation leads not only to process inefficiency but also to substantial increases in processing costs. None of the prior art processes, and particularly none of the U.S. Patents discussed above, deal satisfactorily with the aforesaid problem.

Naturally, it would be highly desirable to provide a process for the conversion of hydrocarbon streams from FCC refinery processes, to MTBE and TAME which overcome the problems of catalyst poisoning as discussed above.

Accordingly, it is the principal object of the present invention to provide a process for the conversion of liquid light hydrocarbon streams to ether-rich additives such as MTBE and TAME in an efficient and economic manner.

It is a particular object of the present invention to provide a process as aforesaid wherein the poisoning of the catalysts used in the etherification process is inhibited.

It is a further object of the present invention to provide a process as aforesaid wherein the liquid light hydrocarbon feedstock fed to the etherification zone is pretreated with a superactivated particulate medium prior to etherification processing in the presence of the catalyst.

It is a still further object of the present invention to provide a process as aforesaid wherein the alumina medium used in the process of the present invention is readily regenerated for further use in the process.

Further objects and advantages of the present invention will appear hereinbelow.

SUMMARY OF THE INVENTION

In accordance with the present invention the foregoing objects and advantages are readily obtained.

The present invention relates to a process for the production of ether-rich additives from light hydrocarbon feedstocks and, more particularly, form light hydrocarbon feedstocks having significant concentrations of nitrogen compounds, mercaptan and water. Such feedstocks include light naphtha cut hydrocarbons from FCC processes. The liquid hydrocarbon feedstocks are passed through a medium for removing the nitrogen compounds, particularly nitrile compounds, mercaptan (thiol) and water from the feedstock so as to form a purified feedstock prior to subjecting the feedstock to etherification process conditions in the presence of the catalyst. In accordance with the present invention, the liquid hydrocarbon feedstock is passed through a superactivated particulate medium where nitrogen compounds, particularly nitrile compounds, mercaptan and water are removed so as to result in a purified feedstock to the etherification zone which is substantially free of nitrogen compounds, mercaptan and water. Suitable particulate media include particles of alumina, silica, zeolite, and mixtures thereof. Such particles are superactivated and, after they are spent, such particles are regenerated, in accordance with the present invention as will be discussed hereinbelow. It has been found in accordance with the present invention that by pretreating the light hydrocarbon feedstock as aforesaid, the rate of poisoning of the catalyst employed in the etherification process is greatly reduced thereby increasing process efficiency while at the same time decreasing processing costs.

The process of the present invention, in its preferred form, provides for a plurality of superactivated particulate mediums wherein the feedstock being treated is passed through one of the plurality of superactivated particulate mediums for purifying same. The purified filtered feedstock is monitored downstream of the particulate medium for sensing when the first medium is spent. When the first medium is spent the feedstock is passed through another of the plurality of particulate mediums so as to allow the process to proceed in a continuous manner. The spent particulate medium is then subjected to a regeneration process in accordance with the present invention.

The spent superactivated particulate medium is regenerated by draining the liquid hydrocarbon feedstock from the medium which is in the form of a bed of porous particles forming interstitial spaces therebetween. The drained bed of particles is thereafter dried with inert gas. In accordance with the present invention, the drained and dried particulate medium is thereafter washed under critical conditions with a superactivating material in a series of steps to remove carbonaceous materials including polymer precursors, to prohibit the formation of polymers and to increase the surface area of the particles. The washed particulate media free of polymers is thereafter dried with inert gas, preferably in a stepwise fashion.

The process of the present invention wherein the feedstock to the etherification reactor is pretreated so as to remove nitrogen compounds, particularly nitrile compounds, mercaptan and water allows for the efficient and economical production of ether-rich additives such as MTBE and TAME by improving the life of the catalyst used in the etherification process. In addition, by providing a process for regenerating the medium used in the pretreatment of the feedstock the overall process of the present invention is efficient and economical to carry out.

BRIEF DESCRIPTION OF THE DRAWINGS

A detailed description of the preferred embodiments of the invention follows, with reference to the accompanying drawings, wherein.

DETAILED DESCRIPTION OF THE INVENTION

Figure 1:
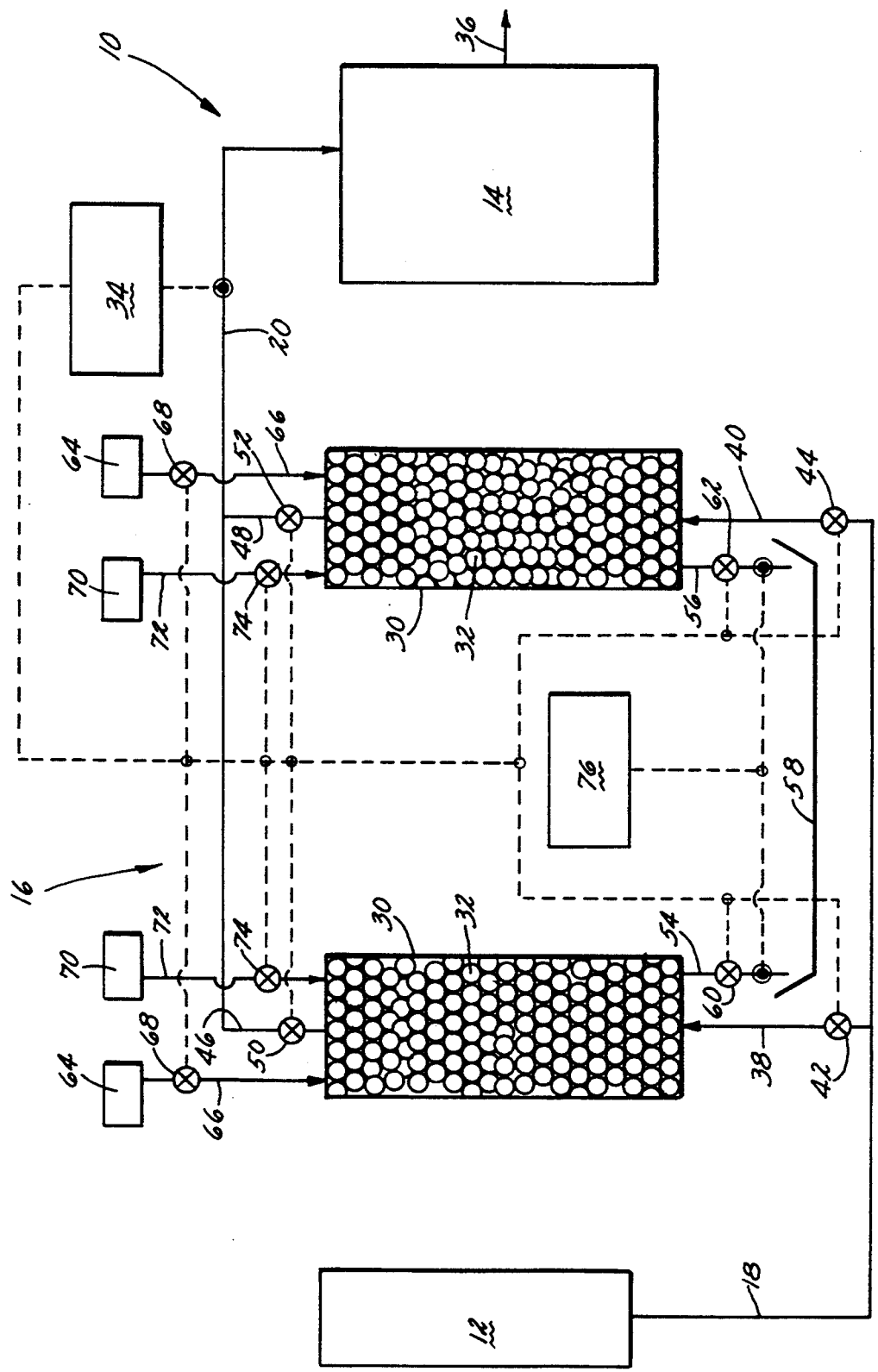
FIG. 1 is a schematic flow diagram illustrating the process of the present invention.

With reference to FIG. 1, the process of the present invention will be described in detail.

A facility 10 for carrying out the conversion of light hydrocarbon feedstocks to an ether-rich additive, particularly TAME and MTBE, is illustrated. For purposes of description the process of the present invention will be described with reference to light hydrocarbon feedstocks obtained form FCC process operations, particularly, light naphtha cut FCC feeds which are cut in the $C_3$-$C_7$ range and preferably $C_4$ and $C_5$ range.

With reference to FIG. 1, the feedstock from the FCC refinery facility 12 is fed to the etherification zone 14 for converting the light hydrocarbon feedstock to an ether-rich additive, particularly, MTBE and TAME. In accordance with the process of the present invention, the feedstock from the FCC process 12 is pretreated prior to feeding same to the etherification zone 14 in purification zone 16 for removing nitrogen compounds, particularly nitriles, mercaptan and water from the light hydrocarbon feedstock produced by the FCC process in zone 12.

In accordance with the present invention, the typical feedstock produced in the FCC refinery facility 12 which is drawn off via line 18 is a light hydrocarbon naphtha feedstock. In accordance with the preferred embodiment of the present invention the light naphtha cut is $C_3$-$C_7$ cut and preferably substantially a $C_4$, $C_5$ cut. The feedstock described above for the etherification zone 14 which is produced in the FCC refinery facility 12 and drawn off via line 18 is characterized by the following composition: isobutene in the range of 10-15 wt. %; isoamylenes in the range of 7-14 wt. %; diolefins in the range of 0.5-1.0 wt. %; a mercaptan concentration in the range of 4-6 ppm; a nitrogen concentration in the range of 17-20 ppm wherein nitriles are present in the range of 15-17 ppm; and water content in the range of about 30-50 ppm.

In accordance with the present invention the feed from the FCC refinery facility 12 is fed to purification zone 16 prior to delivery to the etherification zone 14 for removing nitriles and other nitrogen compounds, mercaptan and water from the feedstock so as to produce a purified feedstock substantially free of nitrogen compounds, particularly nitriles, mercaptan and water for delivery from the purification zone 16 via line 20 to the etherification zone 14. In accordance with the preferred embodiment of the present invention, the purified feedstock from the purification zone 16 which is fed via line 20 to the etherification zone 14 has a total nitrogen content of less than 2 ppm wherein the nitrile content is less than 1 ppm, a total mercaptan content of less than 1 ppm and a water content of less than 1 ppm. It has been found, in accordance with the process of the present invention, that by reducing the nitrogen compounds, mercaptan and water (particularly nitriles) the life of the catalyst used in the etherification process in zone 14 is greatly improved. It has been found that the nitriles in the feedstock decompose in the etherification zone in the presence of water to form amines which deactivate the catalyst employed in the etherification process, that is, poison the catalyst.

The feedstock from the FCC facility 12 is treated in the purification zone 16 by passing the feedstock via line 18 through a particulate medium held in an absorption zone or trap 30. In accordance with the present invention a plurality of traps or zones 30 are employed in the process of the present invention in a manner to be described hereinbelow. The particulate medium employed in the process of the present invention comprises a bed of porous particles 2 which form interstitial spaces therebetween when packed into the absorption zone 30. Suitable porous particles include particles of alumina, silica, zeolite, and mixtures thereof. A particularly suitable alumina medium for use in the process is sold under the trademark SELEXSORB CD and is commercially available from ALCOA. Typically, the feedstock is passed through the medium at a liquid space velocity (LHSV) in the range of about 1.0 to about 5.5 v/v/hr. The process conditions are typically pressure in the range of 100–300 psi and temperature in the range of 50°–200° F.

The purified feedstock leaving the trap or zone 30 is continually monitored by means of a sensor 34 (to be described in detail hereinbelow) in order to insure that the feedstock delivered via line 20 to the etherification zone 14 for processing therein has a total nitrogen content less than 2 ppm wherein the nitriles content is less than 1 ppm, a mercaptan content of less than 1 ppm, and a water content of less than 1 ppm. The purified feedstock from absorption zone 30 is delivered to the etherification zone 14 via line 20 wherein the feedstock is processed under typical etherification conditions in the presence of a catalyst so as to produce ether-rich additives, particularly, MTBE and TAME. The catalyst employed in the etherification zone 14 is in the form an acidic ion exchange resin and a suitable ion exchange resin catalyst is commercially available under the name AMBERLIST from Rohm and Haas or Bayer product K2631. The process conditions in the etherification zone 14 are typically as follows: pressure in the range of 150–300 psi, a temperature in the range of 120°–150° F., a methanol to isoalkene ratio in the range of about 1.05–1.50 mole/mole, and a ratio of $H_2$ to diolefins in the range of about 1.5 to 3.2 moles/moles. The ether-rich additive produced in the etherification zone 14 is discharged via line 36. Depending on the nature of the feedstock to the etherification zone 14, either MTBE or TAME or a mixture of the two is produced and discharged via line 36. For example, if the feed to the etherification zone 14 is substantially rich in $C_4$, the product produced is MTBE. If the feedstock is an FCC cut rich in $C_5$, the resulting ether-rich additive is TAME. If the FCC cut feedstock is a mixture of $C_3$–$C_7$ hydrocarbons, the product of the etherification zone 36 is a mixture of MTBE and TAME compounds.

In accordance with the present invention, it is preferred that the purification zone 16 be provided with a plurality of absorption zones or traps 30 for purifying the feedstock delivered via line 18 from the FCC refining facility 12. By providing a plurality of absorption zones 30 the process can be carried out in a continuous manner wherein the feedstock delivered via line 18 may be treated in one of the absorption zones 30 while the deactivated purifying alumina medium in the other absorption zone 30 is regenerated in accordance with the present invention to a superactivated alumina medium as described hereinbelow.

For purposes of illustration the purification zone 16 is illustrated in FIG. 1 as having two absorption zones 30. Each of the absorption zones 30 are selectively fed with feedstock from line 18 via lines 38 and 40, respectively. Lines 38 and 40 are provided with valves 42 and 44 respectively for selectively feeding the feedstock from line 18 to one or the other of the absorption zones 30 in a manner to be described hereinbelow. The discharge from the absorption zones 30, that is, the purified feedstock, is drawn off via lines 46 and 48 and delivered to feedline 20 for delivery to the etherification zone 14. Valves 50 and 52 are located in lines 46 and 48 respectively and are selectively operable in the manner described hereinbelow.

Sensor 34 is connected to line 20 and monitors the purity of the discharge from the absorption zones 30 in order to assure that the content of nitrogen, nitriles, mercaptan and water in the purified feedstock delivered to the etherification zone 14 meet the purification levels described above. The sensor 34, which is commercially available and the details of which form no part of the present invention, compares the measured values of the nitrogen compounds, nitriles, mercaptan and water in the feedstock in line 20 to a fixed value concentration having the values described above with regard to the feedstock to the etherification zone. By monitoring the discharge from the absorption traps 30 in the manner aforesaid, it can be determined when one of the particulate mediums in one of the absorption traps 30 is spent. Upon sensing that the medium 32 in one of the zones 30 is spent, the sensor, through suitable control means available commercially, may activate valves 42, 44, 50, 52 so as to divert the flow of feed from line 18 to the other of the zones 30 wherein the process can continue in an uninterrupted manner. The spent particulate medium in the zone or trap 30 not in use in the etherification process can then be regenerated in accordance with the present invention in the manner described hereinbelow.

In accordance with the present invention, the spent particulate media is regenerated by first draining any hydrocarbon feed in the absorption zone 30 from the absorption zone via conduits 54 and 56 to sump 58. Lines 54 and 56 are provided with valves 60 and 62 which are selectively operated by the sensor means 34 in a known manner. Once the hydrocarbon medium is drained from the particles within the absorption zone 30, the particles are flushed and dried with an inert gas delivered from a source 64 via line 66 which is provided with valve 68. The inert gas is preferably at a temperature of less than 122° F., more preferably less than 110° F.

The dried particles are then treated in a washing process which superactivates and regenerates the particulate medium for further use in the process. Such treatment removes carbonaceous materials, typically polymer precursors, which inhibit the operation of the porous particles in purifying the liquid hydrocarbon feedstock. This treatment also serves to increase the surface area of the porous particles thereby further improving the activity of the porous particles. Such treatment is preferably carried out at temperatures that avoid the formation and deposition of polymer materials within the particles.

According to the invention, the porous particles are treated with a superactivating material which may preferably be selected from the group consisting of organic solvent, air, mixtures of water vapor and air, and combinations of the foregoing. The temperatures employed during the washing step differ depending upon which superactivating material(s) is used. A discussion of the use of an organic solvent, which may preferably be toluene, follows.

After the porous particles are dried, the particulate medium is subjected to a two-step washing process for regenerating the medium to a superactivated medium for further use in the process. In accordance with the present invention, the dried medium is washed with an organic solvent, preferably toluene, under controlled temperature conditions so as to flush polymer precursors from the medium. It is critical that the temperature in this stage of regeneration be maintained at a temperature less than the temperature which would lead to polymerization of the polymer precursors captive within the medium. Generally, a temperature of less than 122° F. is sufficient; however, a lower temperature may be required depending on the nature of the feedstock treated in the absorption zones 30. With reference to FIG. 1, and for purposes of illustration, the toluene solvent may be delivered from a source 70 via a line 72 provided with valve 74 to the alumina medium for washing same. The used solvent discharged via conduit 54 is monitored by sensor 76 so as to determine when this first step washing operation is completed. For example, it has been found that when flushing the medium with the toluene solvent, the discharged solvent is initially brownish in color as the polymer precursors are removed and the solvent lightens in color as the amount of polymer precursors removed decreases. Therefore, by monitoring the color of the discharged solvent the first step flushing operation can be completed when the discharged solvent runs substantially clear. This color change can be monitored by sensor 76 which can be any suitable commercially available device. Once the polymer precursors have been substantially removed the medium is thereafter washed again with the organic solvent at an elevated temperature of between about 140°–250° F. so as to dissolve any polymers formed in the alumina medium during feedstock purification and the first stage washing. This second stage washing is continued until the discharged solvent again runs substantially clean in the manner described above with regard to the first stage washing and sensor element 76. In accordance with the present invention, the solvent is passed through the particulate medium at a ratio with respect to the volume of porous particles in the zone 30 of greater than 4 volumes of solvent per volume of particles. The washed, superactivated particulate medium is thereafter dried with inert gas supplied via line 66 from source 64 at a temperature of typically between 220° and 500° F. and preferably in two steps from a lower temperature to a higher temperature. After drying, the superactivated alumina medium is cooled and is now ready for use and/or reuse in the etherification process of the present invention.

Alternatively, as set forth above, the particulate medium can be regenerated using mixtures of water vapor and air. It has been found, according to the invention, that superactivation and/or regeneration of the particulate medium with water vapor-air mixtures at the indicated temperatures provides excellent increase in surface area of the particulate medium, thereby greatly increasing and/or restoring the ability of the medium to purify hydrocarbon feedstocks before they are treated with etherification catalysts. As above, the spent particulate medium is preferably dried with an inert gas such as, for example, nitrogen, at temperatures preferably less than 122° F. and more preferably less than 110° F. The dried porous particles are then preferably washed with a mixture of water vapor and air at a temperature preferably greater than about 482° F. (250° C.) and more preferably at a temperature of about between 482° F. and 662° F. so as to remove carbonaceous materials including polymer precursors and to increase the surface area of the particulate medium. Also, it has been found that such treatment, advantageously, does not substantially alter the morphology of the particulate material. In accordance with this embodiment, the surface area of a spent particulate can be 95% restored over a washing time of about between 10 to 24 hours.

Alternatively, air can be used as the superactivating material if the washing step is carried out at a relatively high temperature of about 752° F.

Finally, it has been found that excellent results may also be obtained by combining the use of an organic solvent and mixtures of water vapor and air. In accordance with this embodiment, spent particulate medium is initially dried as above with inert gas. The porous particles are then treated with the organic solvent at a temperature of less than about 122° F. so as to remove polymer precursors from the particles. These washed particles are thereafter again washed, with water vapor and air, at a temperature of about between 482° F. to 662° F. Water vapor and air are preferably provided in a mixture having a molar ratio of air to water vapor of about between 0.1 to 10. This combination of washing with solvent and with water vapor and air mixtures provides excellent results in that polymer precursors are removed and the surface area of the particulate material is regenerated. Of course, using two superactivating materials adds to the cost of the process.

Water vapor and air mixtures may suitably be fed to trap zone 30 in substantially the same manner as organic solvent, as discussed above.

It should be noted that the superactivated particulate medium of the present invention may suitably be provided from commercial porous particles including particulate alumina, silica, zeolite, and mixtures thereof, by treating such commercial porous particles with superactivating materials at the preferred temperatures as set forth above so as to remove undesirable materials from the particles and to increase the surface area thereof.

The sensor 34 operates valves 42, 44, 50, 52, 60, 62, 68, and 74 through suitable control means known in the art (shown by dash lines) for selectively controlling the flow of the feedstock via line 18, inert gas via lines 66 and solvent via lines 72 during the various operation stages of the process of the present invention.

For clarity, the process of the present invention will now be described in a step by step manner with reference to an embodiment wherein the porous particles are alumina and the superactivating material is toluene. With valves 42 and 50 in their open position and valves and 44 and 52 in their closed position, feedstock from FCC refining facility 12 is delivered via line 18 into one of the absorption traps 30 of purification zone 16 for contacting the feed with the alumina medium 32 in the trap 30. The purified discharge from the trap 30 is delivered via line 20 to the etherification zone 14 for processing the same for the production of ether-rich additives. In accordance with the present invention, the feedstock fed to the etherification zone 14 via line 20 has the maximum nitrogen content, nitrile content, mercaptan content and water content set forth above. Sensor 34 continually monitors the purified feedstock in line 20 in order to insure the necessary purity. When the measured values of nitrogen, nitriles, mercaptan and water approaches a fixed value the sensor, sensing the foregoing with associated control means closes valves 42 and 50 and opens valves 44 and 52 so as to divert flow of the feedstock in line 18 to another of the absorption traps 30 within purification zone 16. Thus, the feed to the etherification zone 14 is continuous and non-interrupted. The spent alumina medium in the first absorption trap 30 is thereafter regenerated by the sequential steps of drying with inert gas and two-step washing with organic solvent in the manner described in detail above. When the alumina medium in the second absorption trap becomes spent as determined by sensor 34, valves 44 and 52 are closed and valves 42 and 50 are opened so as to direct the feedstock from line 18 through the now regenerated alumina medium in the first absorption zone 30. The spent alumina in the second zone may now be regenerated in the manner described above. It should be appreciated that the number of absorption zones 30 may be increased as required so as to insure continuous operation of the process and allow for sufficient regeneration of the spent alumina prior to the need for using the spent alumina again in the process scheme.

Of course, the process follows substantially the same steps as set forth above when other porous particles are to be employed, and also when other superactivating materials are to be employed.

As can be seen from the foregoing, the process of the present invention allows for the pretreatment of the feedstock to the etherification zone in a continuous uninterrupted manner. The advantages and superior results obtained by the process of the present invention will be made clear hereinbelow from a consideration of the following illustrative examples.

EXAMPLE I

Figure 2:
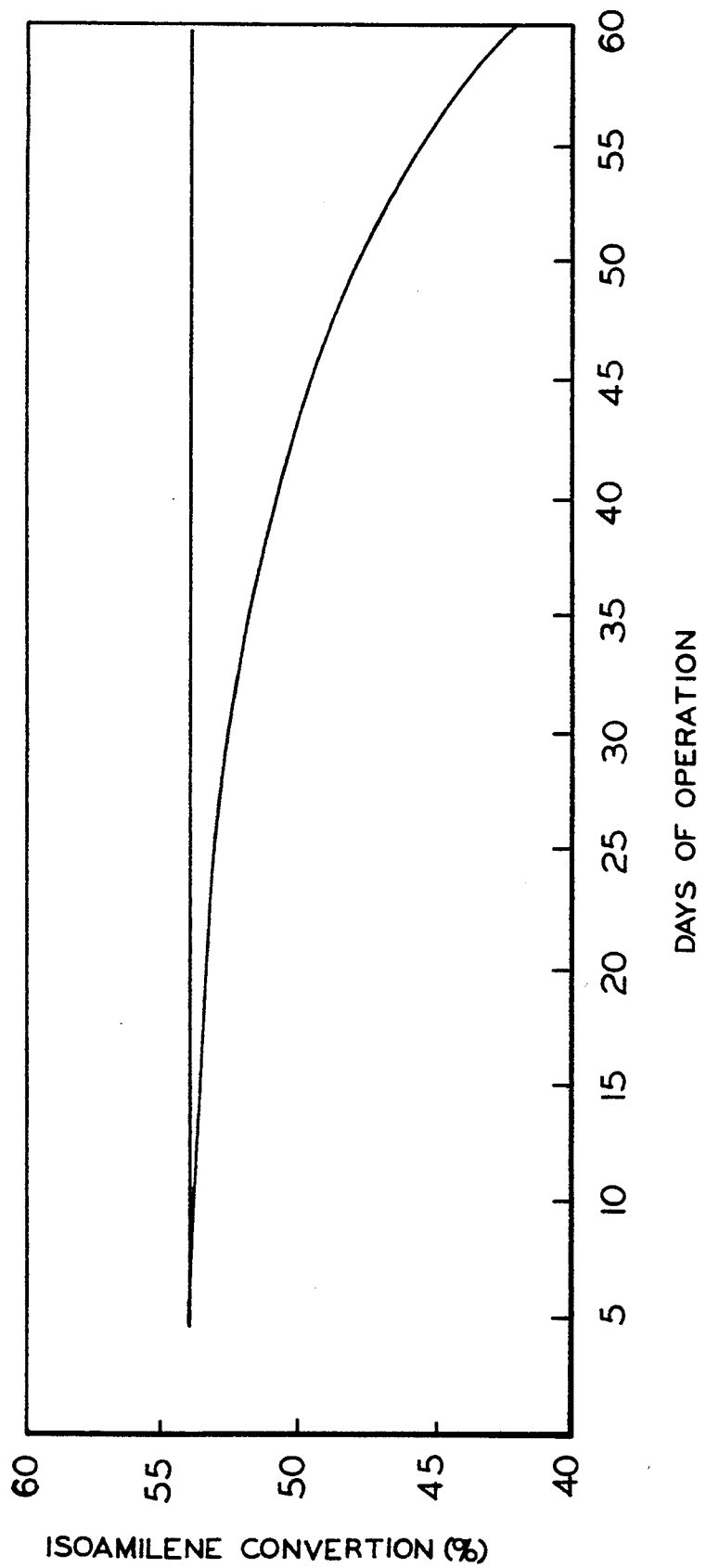
FIG. 2 is a graph demonstrating the adverse effect of nitriles on the acid catalyst activity used in the etherification of light hydrocarbon feedstocks to TAME and demonstrating the advantages of the process of the present invention.

In order to demonstrate the poisoning effect of nitrogen compounds and particularly nitriles such as propionitriles and acetonitriles on the catalyst employed in the etherification process, an untreated FCC feedstock rich in $C_5$ and having the composition set forth in Table I below was subjected to etherification in the presence of an AMBERLIST or Bayer product K2631 ion exchange catalyst under the process and conditions set forth below in Table II. FIG. 2 shows the conversion of the feedstock to the ether-enriched product TAME over time. In order to demonstrate the benefits of pretreatment in accordance with the present invention, the same feedstock was pretreated with a porous alumina bed (SELEXSORB CD alumina sold by ALCOA) to obtain a purified feedstock having the concentration of mercaptan, total nitrogen, and nitrile concentration described below in Table I. This purified feedstock was thereafter subjected to etherification under the same process conditions set forth in Table II. The results of the effect of this feedstock on the feedstock conversion to TAME and thus the deterioration of the catalyst used in the etherification process is illustrated in FIG. 2. It can be seen from FIG. 2 that after 60 days the effectiveness on conversion of the catalyst employed in the etherification process when processing a purified feedstock treated in accordance with the present invention is substantially identical to that obtained from the virgin catalyst while the conversion effectiveness of the catalyst when processing a feedstock which was not treated in accordance with the present invention decreases substantially over time. This example clearly illustrates the effectiveness of the pretreatment of the feedstock in accordance with the present invention to remove nitrogen, nitrile, mercaptan and water in accordance with the present invention.

TABLE I

| FEEDING | UNTREATED | TREATED |
| --- | --- | --- |
| Isobutene (% wt) | 8.20 | 8.00 |
| Isoamylenes (% wt) | 10.10 | 10.10 |
| Diolefins (% wt) | 0.83 | 0.77 |
| Mercaptan (ppm) | 5.00 | less than 1 |
| Nitrogen Total (ppm) | 18.00 | less than 2 |
| Nitriles (ppm) | 17.00 | less than 1 |
| Nitrogen Basic (ppm) | less than 1 | less than 1 |

TABLE II

| | |
| --- | --- |
| Temperature of feeding | 132 degrees F |
| Process Pressure | 175–200 psig |
| LHSV | 2 V/V/hr |

TABLE II-continued

| | |
| --- | --- |
| Ratio of MeOH/ISOALKENES | 1.05 ml/ml |

EXAMPLE II

In order to demonstrate the efficiency of the regeneration process of the present invention for regenerating a porous alumina medium used in the process of the present invention, a spent alumina medium used in the process of the present invention was regenerated with organic solvent (toluene) in accordance with the present invention and compared to a new virgin alumina product. The alumina medium employed was a commercially available alumina medium sold by ALCOA under the name SELEXSORB CD. The spent alumina medium was processed in accordance with the parameters set forth below in Table III. The spent alumina medium was first drained of all liquid hydrocarbon feedstock and thereafter dried with an inert gas, nitrogen, at a temperature of 100° F. for 1 hour. The dried alumina medium was thereafter washed with toluene in the first stage at a temperature of 100° F. for 2.5 hours. The volume of toluene employed in the first step washing operation was in a ratio of 5 volumes of toluene per volume of catalyst. The alumina medium was thereafter subjected to a second washing step at a temperature of 175° F. for an additional period of 2.5 hours. The volume of solvent employed in the second washing step was identical to that employed in the first washing step. The alumina medium was thereafter purged and dried for 4 hours with nitrogen at a temperature of 250° F. and thereafter the temperature of the inert gas was raised to 500° F. and the alumina was dried for 12 hours resulting in a superactivated alumina product in accordance with the present invention.

TABLE III

| | TIME (H) | TEMP (F) | N2(N/H) | TOLUENE (L/H) |
| --- | --- | --- | --- | --- |
| Drying | 1 | 100 | 180–300 | — |
| Washing 1 | 2.5 | 100 | — | 5 |
| Washing 2 | 2.5 | 175 | — | 5 |
| Purging | 4 | 248 | 180–300 | — |
| Desorption | 12 | 500 | 180–300 | — |

Figure 3:
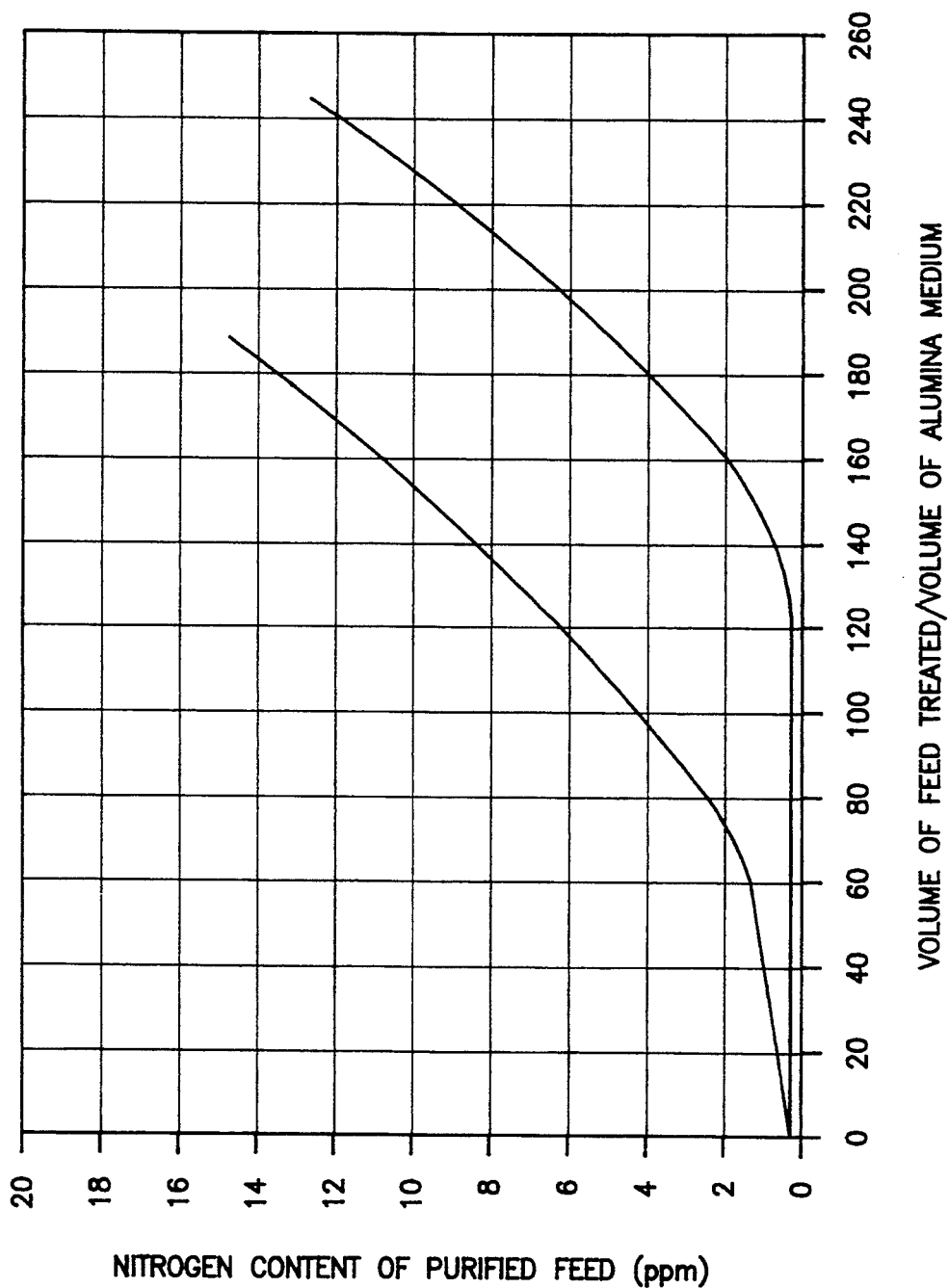
FIG. 3 illustrates the positive effect of the regeneration process of the present invention on the nitrile absorption capabilities of an alumina medium treated in accordance with the process of the present invention.

The regenerated alumina medium was thereafter used to treat the feedstock described above in Example I and compared to a virgin alumina medium used to pretreat the same feedstock under the conditions described above in Example I. FIG. 3 shows the results of this test. It is clear from FIG. 3 that the alumina medium regenerated in accordance with the process of the present invention (curve A) exhibits superior absorption capabilities for nitrogen and nitriles when compared to conventional virgin alumina (curve B).

EXAMPLE III

Tests were run using commercially available alumina (SELEXSORB CD from ALCOA) having a surface area of 305 m²/g and a carbon content of less than 1% wt in a pilot absorbing plant having a capacity of 1 liter. The plant operation conditions were flow between 3.4 to 5 lt/h, LHSV of 5.4 v/v/h (1 cycle to 3.4 v/v/h), pressure of 250 psig, temperature of 100 degrees F. and cycle time of 30–36 hours. After six cycles of operation the alumina was substantially spent.

Another sample of the alumina was placed in a furnace and a water vapor-air mixture was injected to the furnace at different temperatures values. The conditions for the formation of the water vapor-air mixture were as follows:

Ratio liquid water to air: 1:1 (by volume)
absolute pressure of the system: 693 mmHg
Flow of liquid water used: 5 cc/min.
Flow of air used: 5 cc/min.
time of operation: 18 hrs.

Figure 4:
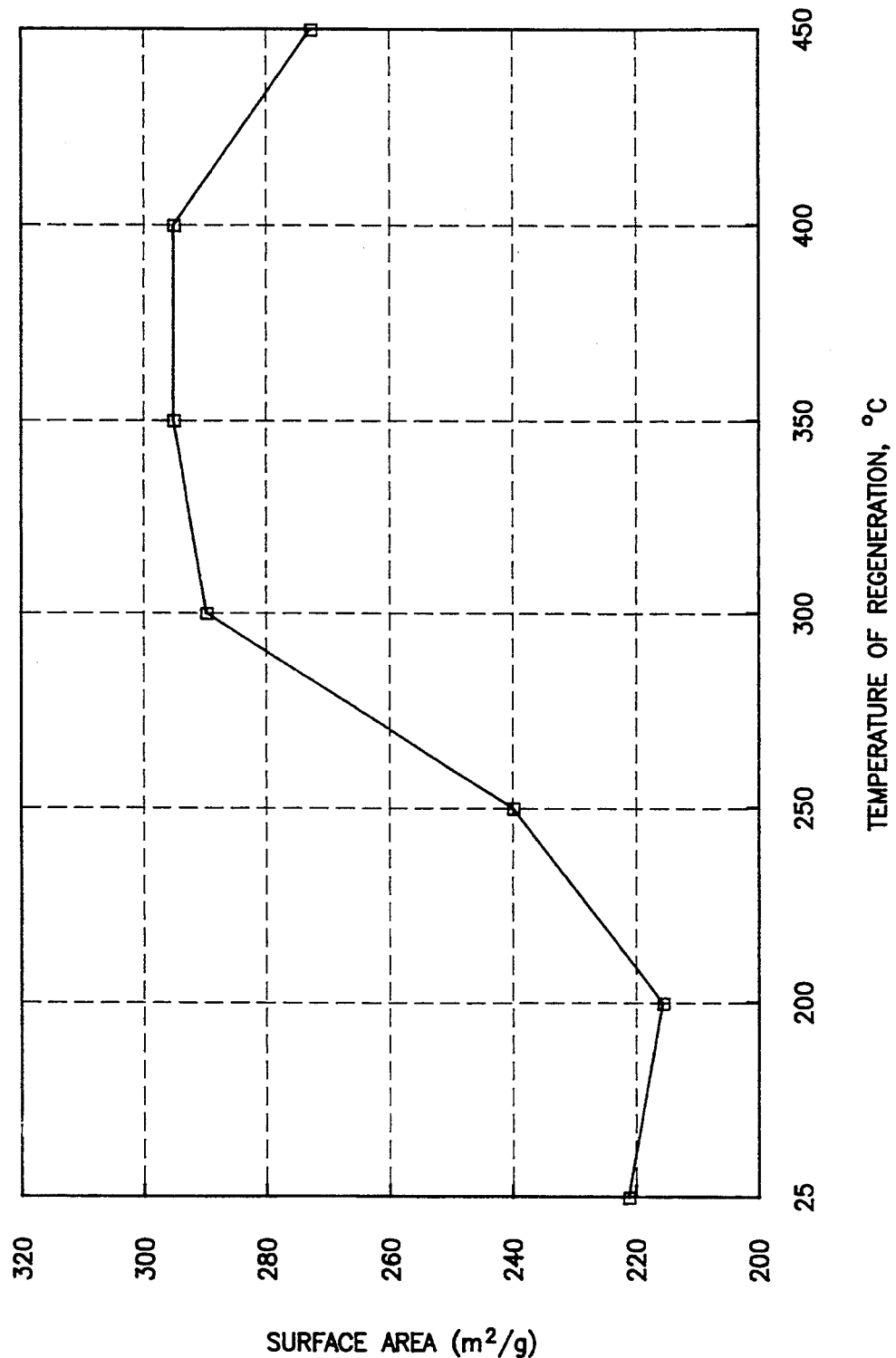
FIG. 4 illustrates the relation between surface area and temperatures of regeneration of superactivated alumina, according to the invention, with a water vapor-air mixture to remove any gum or polymer from the absorbent medium.
Figure 5:
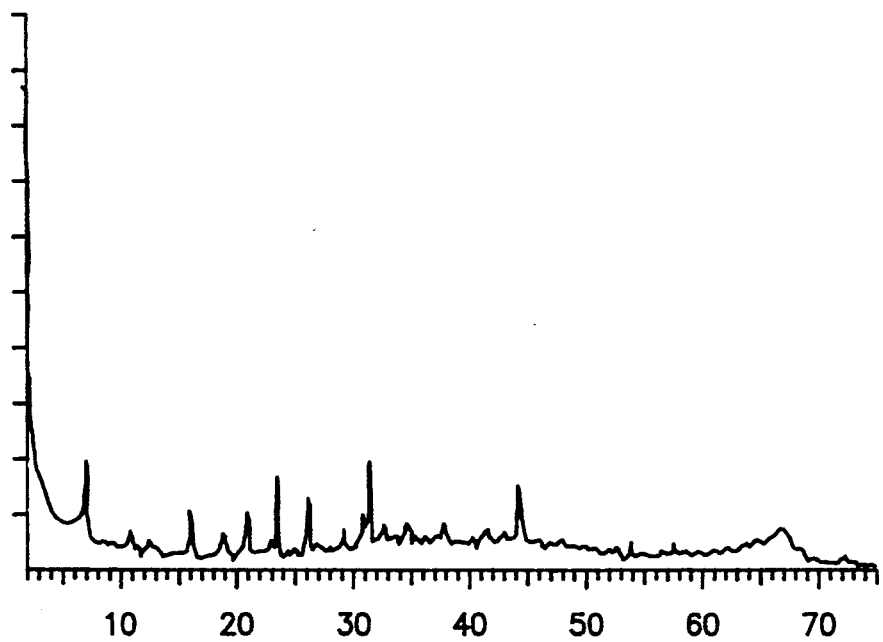
FIG. 5 shows the diffraction spectrum of original commercial alumina.
Figure 6:
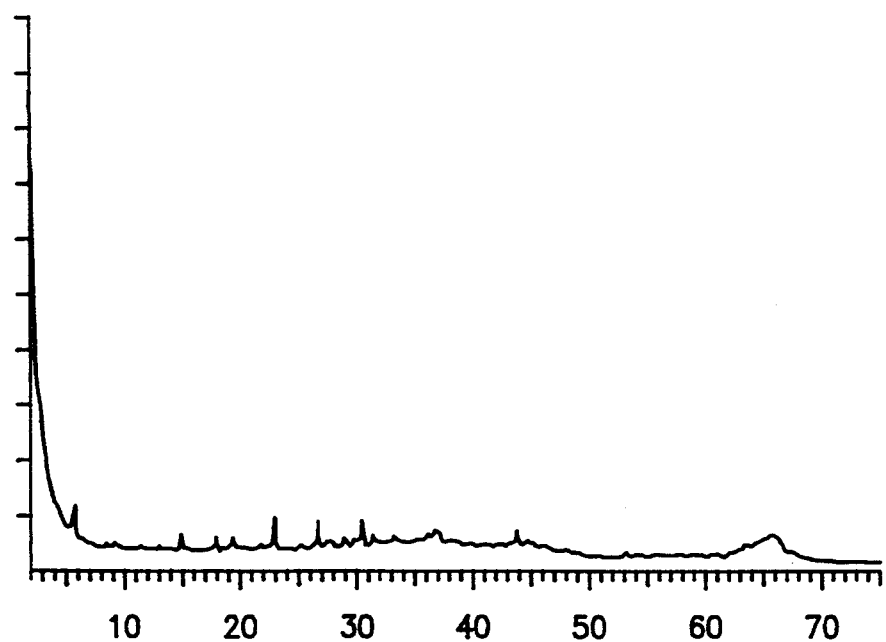
FIG. 6 shows the diffraction spectrum of superactivated alumina after regeneration according to the present invention.

Table IV shows the results of washing the spent alumina with the water vapor-air mixture at different temperatures, and FIGS. 4 and 5 show the X ray spectrum diffraction of the alumina which indicates that there were no significant changes in the morphological structure of the alumina.

TABLE IV

| TEMPERATURE (°C.) | % (Wt) MATERIAL OF CARBON. | SURFACE AREA m2/gr |
|---|---|---|
| 25 | 12.2 | 221 |
| 200 | 11.0 | 215 |
| 260 | 5.9 | 240 |
| 300 | 3.4 | 290 |
| 350 | 2.4 | 295 |
| 400 | 2.0 | 295 |

Furthermore, superactivated alumina regenerated according to the present invention exhibits greatly improved surface area and reduced content of carbonaceous materials, and is therefore quite useful in purifying liquid hydrocarbon feedstocks as described herein.

As can be seen from the foregoing, the process of the present invention provides for an effective and economical process for producing ether-rich additives such as TAME and MTBE from light hydrocarbon feedstocks.

This invention may be embodied in other forms or carried out in other ways without departing for the spirit or essential characteristics thereof. The present embodiment is therefore to be considered as in all respects illustrative and not restrictive, the scope of the invention being indicated by the appended claims, and all changes which come within the meaning and range of equivalency re intended to be embraced therein.

What is claimed is:

1. A process for the production of an ether-rich additive, comprising:
   (a) providing a liquid hydrocarbon feedstock containing nitrogen compounds, mercaptan and water;
   (b) providing a particulate medium of porous particles selected from the group consisting of particles of alumina, silica, zeolite and mixtures thereof;
   (c) passing said liquid hydrocarbon feedstock through said particulate medium so as to remove nitrogen compounds, mercaptan and water so as to form a purified feedstock substantially free of nitrogen compounds, mercaptan and water wherein the particulate medium becomes poisoned with the nitrogen compounds;
   (d) treating said purified feedstock with a catalyst under etherification process conditions in the presence of an isoalkene in an alcohol so as to produce an ether rich additive;
   (e) regenerating said particulate medium from said poisoned porous particles to form a superactivated particulate medium by the following steps:
      (1) drying said porous particles by passing an inert gas through said porous particles at a temperature of not greater than about 122° F.;
      (2) washing said porous particles with an organic solvent at a temperature of less than about 122° F. so as to flush polymer precursors from said porous particles while substantially avoiding formation of polymers within said porous particles;
      (3) sensing when said porous particles are substantially free of said polymer precursors; and
      (4) thereafter further flushing said porous particles with said organic solvent at a temperature of about between 140° F. to 250° F. so as to dissolve polymers within said porous particles while maintaining said solvent in a liquid phase.

2. A process according to claim 1, wherein said sensing comprises the steps of:
   (a) measuring the concentration of nitrogen compounds, mercaptan and water in said purified feedstock downstream of said one superactivated particulate medium; and
   (b) comparing the measured value to a fixed value concentration of nitrogen compounds, mercaptan and water.

3. A process according to claim 1, wherein said inert gas is nitrogen.

4. A process for the production of an ether-rich additive, comprising:
   (a) providing a liquid hydrocarbon feedstock containing nitrogen compounds, mercaptan and water;
   (b) providing a particulate medium of porous particles selected from the group consisting of particles of alumina, silica, zeolite and mixtures thereof;
   (c) passing said liquid hydrocarbon feedstock through said particulate medium so as to remove nitrogen compounds, mercaptan and water so as to form a purified feedstock substantially free of nitrogen compounds, mercaptan and water wherein the particulate medium becomes poisoned with the nitrogen compounds;
   (d) treating said purified feedstock with a catalyst under etherification process conditions in the presence of an isoalkene in an alcohol so as to produce an ether-rich additive;
   (e) regenerating said particulate medium from said poisoned porous particles to form a superactivated particulate medium by the following steps:
      (1) drying said porous particles by passing an inert gas through said porous particles at a temperature of not greater than about 122° F.; and
      (2) washing said porous particles with a mixture of water vapor and air at a temperature of at least about 482° F. so as to remove carbonaceous materials from said porous particles and to increase surface area of said porous particles without substantially modifying morphology structure of said porous particles until said porous particles are substantially free of said carbonaceous materials.

5. A process according to claim 4, wherein said washing is carried out at a temperature of about between 482° F. to 662° F.

6. A process according to claim 4, wherein said mixture of water vapor to air is supplied at a molar ratio of air to water vapor of about between 0.1 to 10.

7. A process for the production of an ether-rich additive, comprising:
   (a) providing a liquid hydrocarbon feedstock containing nitrogen compounds, mercaptan and water;

(b) providing a particulate medium of porous particles selected from the group consisting of particles of alumina, silica, zeolite and mixtures thereof;

(c) passing said liquid hydrocarbon feedstock through said particulate medium so as to remove nitrogen compounds, mercaptan and water so as to form a purified feedstock substantially free of nitrogen compounds, mercaptan and water wherein the particulate medium becomes poisoned with the nitrogen compounds;

(d) treating said purified feedstock with a catalyst under etherification process conditions in the presence of an isoalkene in an alcohol so as to produce an ether-rich additive;

(e) regenerating said particulate medium from said poisoned porous particles to form a superactivated particulate medium by the following steps:

(1) drying said porous particles by passing an inert gas through said porous particles at a temperature of not greater than about 122° F.; and (2) washing said porous particles with air at a temperature of at least about 752° F. so as to remove carbonaceous materials from said porous particles and to increase surface area of said porous particles without substantially modifying morphology structure of said porous particles until said porous particles are substantially free of said carbonaceous materials.

8. A process for the production of an ether-rich additive, comprising:

(a) providing a liquid hydrocarbon feedstock containing nitrogen compounds, mercaptan and water;

(b) providing a particulate medium of porous particles selected from the group consisting of particles of alumina, silica, zeolite and mixtures thereof;

(c) passing said liquid hydrocarbon feedstock through said particulate medium so as to remove nitrogen compounds, mercaptan and water so as to form a purified feedstock substantially free of nitrogen compounds, mercaptan and water wherein the particulate medium becomes poisoned with the nitrogen compounds;

(d) treating said purified feedstock with a catalyst under etherification process conditions in the presence of an isoalkene in an alcohol so as to produce an ether-rich additive;

(e) regenerating said particulate medium from said poisoned porous particles to form a superactivated particulate medium by the following steps:

(1) drying said porous particles by passing an inert gas through said porous particles at a temperature of not greater than about 122° F.;

(2) washing said porous particles with an organic solvent at a temperature of less than about 122° F. so as to flush polymer precursors from said porous particles while substantially avoiding formation of polymers within said porous particles;

(3) sensing when said porous particles are substantially free of said polymer precursors; and (4) thereafter further flushing said porous particles with a mixture of water vapor and air at a temperature of at least about 482° F. to further remove carbonaceous materials including polymer precursors from said porous particles and to increase surface area of said porous particles without substantially modifying morphology structure of said porous.

9. A process according to claim 8 wherein said organic solvent is toluene.

10. A process according to claim 8, wherein said further flushing step is carried out at a temperature of about between 482° F. and 662° F.

11. A process according to claim 8, wherein the step of passing said liquid hydrocarbon feedstock through said superactivated particulate medium is carried out under the following conditions:
pressure in the range of about between 100-300 psi, temperature in the range of about between 50°-200° F. in a liquid space velocity (LHSV) in the range of about between 1.0-5.5 V/V/hr.

12. A process according to claim 8, wherein the etherification process conditions comprise treating said purified feedstock at a pressure in the range of about between 150-300 psi, a temperature in the range of about between 120°-150° F,. a methanol to isoalkene ratio in the range of about between 1.05-1.50 mole/mole, and a ratio of $H_2$ to diolefins in the range of about 1.5 to about 3.2 mole/mole.

13. A process according to claim 8, further including the steps of:

(a) providing a plurality of superactivated particulate mediums;

(b) passing said liquid hydrocarbon feedstock through one of said plurality of superactivated particulate mediums;

(c) sensing when said one of said plurality of superactivated particulate mediums is spent;

(d) thereafter passing said liquid hydrocarbon feedstock through another of said plurality of superactivated particulate mediums; and (e) regenerating said spent superactivated particulate medium.

14. A process according to claim 8, wherein said nitrogen compounds are in the form of nitriles.

15. A process according to claim 8, wherein said liquid hydrocarbon feedstock comprises a hydrocarbon stream of an FCC light naphtha cut.

16. A process according to claim 15, wherein the light naphtha cut is a $C_3$-$C_7$ cut.

17. A process according to claim 16, wherein said light naphtha cut is substantially a $C_4$ and $C_5$ cut.

18. A process according to claim 8, wherein said catalyst is an ion exchange resin catalyst.

19. A process according to claim 8, wherein said ether-rich additive is MTBE, TAME or mixtures thereof.

20. A process according to claim 8, wherein said liquid hydrocarbon feedstock is an FCC $C_3$-$C_7$ feedstock having a nitrogen content of grater than 2 ppm.

21. A process according to claim 20, wherein the feedstock has a water content of greater than about 2 ppm.

22. A process according to claim 21, wherein said liquid hydrocarbon feedstock has a mercaptan content of greater than 1 about ppm.

23. A process according to claim 8, wherein said purified feedstock has nitrogen content of less than about 2 ppm, a mercaptan content of less than about 1 ppm and a water content of less than about 1 ppm.

24. A process according to claim 8, wherein said liquid hydrocarbon feedstock contains from about 10-15 wt. % isobutene, from about 7-14% isoamylenes, from about 0.5-1.0 wt. % diolefins, and from about 17 to about 20 ppm nitrogen, and wherein about 15-17 pm of said nitrogen is in the form of nitriles.

* * * * *